US009517135B2

(12) United States Patent
Ramos et al.

(10) Patent No.: US 9,517,135 B2
(45) Date of Patent: Dec. 13, 2016

(54) CONDYLAR PROSTHESIS FOR A TEMPORO-MANDIBULAR JOINT (71) Applicants: UNIVERSITE DE BORDEAUX, Talence (FR); CENTRE NATIONAL DE LA RECHERCHE SCIENTIFIQUE, Paris (FR); UNIVERSIDADE DE AVEIRO, Aveiro (PT)

(72) Inventors: Antonio Ramos, Ilhavo (PT); Michel Mesnard, Bordeaux (FR)

(73) Assignees: UNIVERSITE DE BORDEAUX, Talence (FR); CENTRE NATIONAL DE LA RECHERCHE SCIENTIFIQUE, Paris (FR); UNIVERSIDADE DE AVEIRO, Aveiro (PT)

( * ) Notice: Subject to any disclaimer, the term of this patent is extended or adjusted under 35 U.S.C. 154(b) by 0 days.

(21) Appl. No.: 14/419,717

(22) PCT Filed: Aug. 5, 2013

(86) PCT No.: PCT/FR2013/051882
§ 371 (c)(1),
(2) Date: Feb. 5, 2015

(87) PCT Pub. No.: WO2014/023903
PCT Pub. Date: Feb. 13, 2014

(65) Prior Publication Data
US 2015/0182340 A1    Jul. 2, 2015

(30) Foreign Application Priority Data
Aug. 6, 2012 (FR) ...................... 12 57637

(51) Int. Cl.
A61F 2/02 (2006.01)
A61F 2/30 (2006.01)

(52) U.S. Cl.
CPC .... *A61F 2/3099* (2013.01); *A61F 2002/30024* (2013.01); *A61F 2002/3054* (2013.01);
(Continued)

(58) Field of Classification Search
CPC ..................... A61F 2/3099; A61F 2002/30125
(Continued)

(56) References Cited

U.S. PATENT DOCUMENTS 3,064,645 A * 11/1962 Ficat .......................... A61F 2/32
123/23
3,765,034 A * 10/1973 Johnston ............ A61B 17/1753
606/98
(Continued)

FOREIGN PATENT DOCUMENTS

| EP | 0 524 874 | 1/1993 |
| FR | 2 558 721 | 8/1985 |
| WO | 97/11651 | 4/1997 |

OTHER PUBLICATIONS

International Search Report dated Feb. 18, 2014, corresponding to PCT/FR2013/051882.

*Primary Examiner* — Alvin Stewart
(74) *Attorney, Agent, or Firm* — Young & Thompson (57) ABSTRACT The condylar prosthesis (10) for a temporo-mandibular joint includes a mandibular implant (12), which is intended to be rigidly attached to the branch of a mandible, and a joint head (16), which is intended to serve as a replacement mandibular condyle, the mandibular implant (12) including an anchoring stem (14) permitting the use of an intramedullary connection in the summit of the branch of the mandible, and the distal end of the anchoring stem (14) being offset towards the front of the prosthesis (10) with respect to the
(Continued)

joint head (16) and in a median plane of the prosthesis (10), the condylar prosthesis (10) being characterized in that the anchoring stem (14) follows a curved profile along its length and in the median plane of the prosthesis, the direction of curvature of the anchoring stem being oriented towards the front of the prosthesis.

21 Claims, 4 Drawing Sheets (52) U.S. Cl.
CPC ......... *A61F 2002/30125* (2013.01); *A61F 2002/30377* (2013.01); *A61F 2002/30403* (2013.01); *A61F 2002/30433* (2013.01); *A61F 2002/30578* (2013.01); *A61F 2002/30649* (2013.01); *A61F 2002/30878* (2013.01); *A61F 2002/30991* (2013.01); *A61F 2002/30993* (2013.01)

(58) Field of Classification Search
USPC ............ 623/17.17, 21.13, 19.12, 20.22, 20.36,623/20.35, 21.12, 22.4, 23.15, 23.39, 23.4,623/21.15, 20.11–20.13, 19.11
See application file for complete search history.

(56) References Cited

U.S. PATENT DOCUMENTS

| | | | | |
|---|---|---|---|---|
| 3,965,490 A * | 6/1976 | Murray | A61F 2/3662 | 623/23.29 |
| 4,004,300 A * | 1/1977 | English | A61F 2/3609 | 623/22.17 |
| D248,665 S * | 7/1978 | Homsy | 623/17.17 | |
| 4,101,985 A * | 7/1978 | Baumann | A61F 2/30739 | 606/67 |
| 4,141,088 A * | 2/1979 | Treace | A61F 2/32 | 606/62 |
| 4,279,041 A * | 7/1981 | Buchholz | A61F 2/32 | 403/123 |
| 4,279,042 A * | 7/1981 | Andriacchi | A61F 2/36 | 623/23.15 |
| 4,283,799 A * | 8/1981 | Pratt, Jr. | A61F 2/30907 | 623/23.37 |
| 4,658,808 A * | 4/1987 | Link | A61F 2/30942 | 33/511 |
| 4,693,722 A * | 9/1987 | Wall | A61F 2/30965 | 623/17.17 |
| 4,713,077 A * | 12/1987 | Small | A61B 17/176 | 128/898 |
| 4,726,808 A | 2/1988 | Collins | | |
| 4,778,472 A * | 10/1988 | Homsy | A61F 2/3099 | 623/17.17 |
| 4,895,573 A * | 1/1990 | Koeneman | A61F 2/30965 | 606/89 |
| 4,917,701 A * | 4/1990 | Morgan | A61F 2/3099 | 623/17.17 |
| 5,405,393 A * | 4/1995 | Falkenstrom | A61F 2/3099 | 623/17.17 |
| 5,405,401 A * | 4/1995 | Lippincott, III | A61F 2/4241 | 623/21.15 |
| 5,489,305 A | 2/1996 | Morgan | | |
| 5,507,829 A * | 4/1996 | Thongpreda | A61F 2/30767 | 623/22.41 |
| 5,549,680 A * | 8/1996 | Gordon | A61F 2/3099 | 623/17.17 |
| 5,658,352 A * | 8/1997 | Draenert | A61B 17/8808 | 623/22.4 |
| 5,674,297 A * | 10/1997 | Lane | A61F 2/4241 | 623/21.16 |
| 5,800,553 A * | 9/1998 | Albrektsson | A61B 17/1668 | 606/65 |
| 5,858,020 A * | 1/1999 | Johnson | A61F 2/389 | 606/78 |
| 5,871,549 A * | 2/1999 | Jayashankar | A61L 27/50 | 623/22.4 |
| 5,989,292 A * | 11/1999 | van Loon | A61F 2/3099 | 623/17.17 |
| 6,030,417 A * | 2/2000 | Bresler | A61F 2/36 | 623/23.15 |
| 6,120,544 A * | 9/2000 | Grundei | A61F 2/30907 | 16/23 |
| 6,132,466 A * | 10/2000 | Hoffman | A61F 2/3099 | 623/17.17 |
| 6,136,035 A * | 10/2000 | Lob | A61F 2/3662 | 623/20.15 |
| 6,217,616 B1 * | 4/2001 | Ogilvie | A61F 2/3804 | 623/20.11 |
| 6,224,634 B1 * | 5/2001 | Keller | A61F 2/36 | 623/23.11 |
| 6,454,808 B1 * | 9/2002 | Masada | A61F 2/4241 | 623/21.13 |
| 6,485,520 B1 * | 11/2002 | Hubach | A61F 2/4261 | 623/21.13 |
| 6,706,073 B2 * | 3/2004 | Draenert | A61F 2/36 | 623/22.46 |
| 6,709,459 B1 * | 3/2004 | Cooney, III | A61B 17/15 | 623/20.11 |
| 7,160,329 B2 * | 1/2007 | Cooney, III | A61F 2/3804 | 623/20.11 |
| 7,494,509 B1 * | 2/2009 | Hershberger | A61F 2/3662 | 623/22.4 |
| 7,537,618 B2 * | 5/2009 | Collazo | A61F 2/4014 | 623/19.11 |
| 7,585,327 B2 * | 9/2009 | Winslow | A61F 2/4003 | 623/19.11 |
| 7,601,175 B2 * | 10/2009 | Feigenwinter | A61B 17/8071 | 623/17.17 |
| 7,854,767 B2 * | 12/2010 | May | A61B 17/744 | 623/18.11 |
| 7,875,083 B2 * | 1/2011 | Sudmann | A61B 17/17 | 623/23.29 |
| 7,887,586 B2 * | 2/2011 | Linares | A61F 2/0811 | 606/247 |
| 7,976,580 B2 * | 7/2011 | Berger | A61F 2/4241 | 623/21.13 |
| 8,021,431 B1 * | 9/2011 | Townley | A61F 2/4241 | 623/21.11 |
| 8,052,757 B1 * | 11/2011 | Scheker | A61F 2/4261 | 623/21.13 |
| 8,177,852 B2 * | 5/2012 | Mcminn | A61F 2/3859 | 623/22.44 |
| 8,366,785 B1 * | 2/2013 | Townley | A61F 2/4241 | 623/21.11 |
| 8,562,689 B2 * | 10/2013 | Scheker | A61F 2/4261 | 623/21.11 |
| 8,852,288 B2 * | 10/2014 | Hoffman | A61F 2/36 | 623/22.11 |
| 9,051,639 B2 * | 6/2015 | McEntire | A61F 2/32 | |
| 2001/0025199 A1 * | 9/2001 | Rauscher | A61F 2/4241 | 623/21.13 |
| 2003/0163202 A1 * | 8/2003 | Lakin | A61F 2/32 | 623/22.15 |
| 2003/0187511 A1 * | 10/2003 | Ball | A61F 2/4261 | 623/21.13 |
| 2003/0187514 A1 * | 10/2003 | McMinn | A61F 2/3859 | 623/22.44 |
| 2005/0119757 A1 * | 6/2005 | Hassler | A61F 2/4261 | 623/21.15 |
| 2005/0171613 A1 * | 8/2005 | Sartorius | A61F 2/4261 | 623/21.13 |
| 2006/0030946 A1 * | 2/2006 | Ball | A61F 2/4261 | 623/21.13 |
| 2006/0116771 A1 * | 6/2006 | Cooney, III | A61F 2/3804 | 623/20.11 |
| 2006/0142866 A1 * | 6/2006 | Baratz | A61F 2/3804 | 623/20.11 |

(56) References Cited

U.S. PATENT DOCUMENTS

| | | | |
|---|---|---|---|
| 2007/0250176 A1* | 10/2007 | Ragbir | A61F 2/3601 623/23.15 |
| 2008/0009951 A1* | 1/2008 | Hodge | A61B 17/1753 623/20.35 |
| 2008/0051909 A1* | 2/2008 | Wolfe | A61F 2/4261 623/21.12 |
| 2008/0114461 A1* | 5/2008 | Collazo | A61F 2/4014 623/19.14 |
| 2008/0200990 A1* | 8/2008 | McTighe | A61F 2/36 623/22.42 |
| 2008/0288079 A1* | 11/2008 | Leibel | A61F 2/3804 623/20.11 |
| 2009/0043397 A1* | 2/2009 | Park | A61B 17/74 623/23.11 |
| 2009/0054992 A1* | 2/2009 | Landes | A61B 17/1682 623/21.18 |
| 2009/0112329 A1* | 4/2009 | Craig | A61B 17/72 623/19.14 |
| 2009/0138092 A1* | 5/2009 | Johnston | A61F 2/3099 623/17.17 |
| 2009/0222102 A1* | 9/2009 | Deffrennes | A61F 2/30942 623/17.17 |
| 2009/0254189 A1* | 10/2009 | Scheker | A61F 2/4261 623/21.11 |
| 2009/0312839 A1* | 12/2009 | Scheker | A61F 2/3804 623/20.11 |
| 2009/0319050 A1* | 12/2009 | Palmer | A61F 2/4261 623/21.12 |
| 2010/0042222 A1* | 2/2010 | Song | A61C 8/0092 623/17.17 |
| 2010/0312354 A1* | 12/2010 | Bandoh | A61F 2/36 623/23.15 |
| 2011/0082560 A1* | 4/2011 | Copf | A61F 2/36 623/20.36 |
| 2011/0125274 A1* | 5/2011 | Bartel | A61F 2/3804 623/20.11 |
| 2011/0137422 A1 | 6/2011 | Wilkes | |
| 2012/0136453 A1* | 5/2012 | Scheker | A61F 2/4261 623/21.12 |
| 2013/0226307 A1* | 8/2013 | McEntire | A61F 2/3601 623/22.4 |
| 2013/0338784 A1* | 12/2013 | Pallia | A61F 2/4241 623/21.13 |
| 2014/0121779 A1* | 5/2014 | Gonzalez-Hernandez | A61F 2/3804 623/20.12 |
| 2015/0182340 A1* | 7/2015 | Ramos | A61F 2/3099 623/17.17 |
| 2015/0342745 A1* | 12/2015 | Roux | A61F 2/4241 623/21.15 |

* cited by examiner

CONDYLAR PROSTHESIS FOR A TEMPORO-MANDIBULAR JOINT

This invention relates to a condylar prosthesis for a temporomandibular joint.

The bilateral temporomandibular joint is a dual synovial joint that is enclosed in an articular capsule and that makes it possible to connect the condyle of the mandible to the cavitas glenoidalis or glenoid fossa of the temporal bone of the skull by means of a fibrocartilaginous disc.

In addition, this joint is driven by various muscles: masticatory muscles, such as the temporal muscle, the masseter muscle, the pterygoid muscles, and the suprahyoid muscles and the infrahyoid muscles, so as to obtain the movements of propulsion or retropulsion, of lowering or raising the mandible, and diduction.

Anatomically, two joints operate in synergy on both sides of the skull for making possible the above-mentioned movements of the mandible and for performing the functions of swallowing, salivating, chewing, phonation and yawning.

As for other joints, the functions allowed by the temporomandibular joint are able to be affected over the long term by different pathologies or more abruptly following trauma.

The pathology most often responsible for a reduction in the functions of this joint is osteoarthritis, with this degeneration being able to be caused or aggravated by the stress currently noted in younger and younger individuals.

In order to provide an order of magnitude, it is believed that each year in the United States, more than one million new patients suffer from temporomandibular joint problems and that, among these pathological cases, 2 to 3% require a reconstruction.

The degeneration of this joint can also have as its origin a poor dental occlusion, a parafunction consisting in gritting or grinding the teeth, a malfunction in the play of the agonistic and antagonistic muscles, a reduction of the physiological rest phase of the muscles, muscular cramps, or a poor position of the tongue, leading to poor saliva deglutition.

In a first stage of deterioration of articular functions, the amplitudes of movements of the mandible relative to the skull decrease, and only the physical and/or psychological comfort of the patients is affected.

However, at a much higher stage, an ossification can occur that tends to be a cause of infirmity because of the mandible becoming completely immobilized in the cavitas glenoidalis.

In addition, and starting from the first stage of the deterioration, the affected individuals may feel significant pain.

Also, to relieve the patients and to stop the degeneration of the joint, different approaches have been developed.

According to a first rehabilitation method, an articular interface is produced during surgical intervention by inserting between the mandibular condyle and the glenoid fossa a cupule, in particular made of a biomaterial, or a bit of muscle taken from the patient.

This first method can offer satisfactory results in some cases. However, the rate of recurrence is greater than 50% when the intervention follows an infection or a degenerative illness.

In addition, the surgical intervention is technically difficult, and managing after-effects following the samples taken prolongs the post-operative period.

Facing the failures and drawbacks of this first rehabilitation method, implanting a prosthesis constitutes a better approach, as much for caring for adult patients as for caring for children, for example in the case of irreversible trauma and despite incomplete growth.

There are different categories of prostheses for rehabilitating a temporomandibular joint: the prostheses that are substituted in the cavitas glenoidalis and on the temporal slope, the prostheses that replace the mandibular condyle, and the complete prostheses for the combined replacement of the temporal articular surface and the condyle.

This invention pertains more particularly to the replacement of the mandibular condyle, but it also thereby relates to the design of the complete prostheses.

The installation of a prosthesis is a complex operation because of the nature of the bone structures adjacent to the temporomandibular joint.

Also, the geometry and the material of the prosthesis play a prominent role in the quality and the service life of the prosthetic joint.

Currently, only two models of complete prostheses of the temporomandibular joint are available on the market and approved by the cognizant authorities such as the Food and Drug Administration.

Figure 1A:
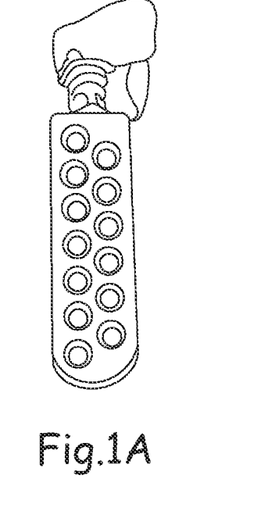
FIGS. 1A and 1B show complete prostheses according to the prior art.
Figure 1B:
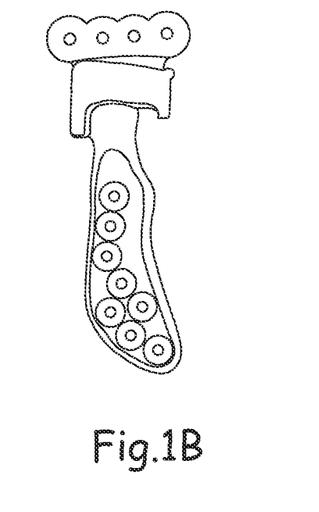

In these two prosthesis models, illustrated by FIGS. 1A and 1B, the substitute condyle is supported by a mandibular implant fixed on the lateral face of the mandibular branch using surgical screws.

As FIGS. 1A and 1B illustrate, the mandibular implant of these prostheses of the prior art comprises a flat and solid attachment plate without shapes that are truly adapted to the bony profile of the lateral face of the mandibular branch.

Consequently, the mandibular implant is never integrally in contact with the lateral face of the mandibular branch, and the thickness of the implant imparts to it mechanical capacities, such as rigidity, which are much greater than those of the mandibular branch, which increases the risks of micromovements of the prosthesis and the malocclusion.

From an anatomical standpoint, this solid design of the mandibular implant decreases the patient's comfort, in particular by an inconvenience of the insertion of the masseter muscle that is greatly aggravated by chewing.

In addition, from a biomechanical standpoint, the different holding openings provided in the mandibular implant do not make it possible to correctly distribute the screws during the surgical intervention and in particular in such a way as to take into account the offsetting of the load exerted on the substitute condyle and to be able to withstand the torque thus exerted on the latter.

After several years of use of these prostheses, it has been found that the non-optimized load transfer to the bony tissue generates:

A concentration of stresses in the near zone of the condyle and the first screw, as well as a random osteointegration in the central zone, An increase in the rigidity of the prosthesized mandible and, consequently, a high risk of degeneration of adjacent bony tissue, A reduction in the variation of the inter-condyle distance under load, and, consequently, a disruption of the dental occlusion.

These negative effects are likely to cause, over the more or less long term, various problems for the patients.

These problems can be reflected by a limitation of certain mobilities of the mandible, by persistent pain or inflammatory phenomena, or, sometimes, by a rupture of the prosthesis or the mandibular connection requiring surgical intervention and optionally the installation of a new prosthesis.

Also, from a general standpoint, the different prostheses that are used even now comprise mandibular implants with empirical designs, essentially based on data of descriptive anatomy and that do not make it possible to produce satisfactory results in terms of quality and reliability over time.

An ideal approach would be to design the prosthesis and its mandibular implant based on the anatomy of each patient and outer shapes of the patient's mandible.

This approach is obviously not viable because of the high costs and means that should be mobilized for the anatomical analysis of the patient's mandible, for the individualized production of the prosthesis, and for its installation.

The purpose of this invention is to remedy the various drawbacks encountered with the prostheses of the prior art.

For this purpose, the invention has as its object a condylar prosthesis for a temporomandibular joint, with the condylar prosthesis comprising a mandibular implant, designed to be made integral with the branch of a mandible, and a joint head, designed to serve as a substitute mandibular condyle, with the mandibular implant comprising an anchoring stem making possible the use of an intramedullary connection in the top of the branch of the mandible, and with the distal end of the anchoring stem being offset toward the front of the prosthesis relative to the joint head and in a median plane of the prosthesis.

According to the invention, the condylar prosthesis is characterized in that the anchoring stem follows a curved profile in its length and in the median plane of the prosthesis, with the direction of the curvature of the anchoring stem being oriented toward the front of the prosthesis.

Advantageously, the combination of the offsetting of the distal end of the anchoring stem and the curvature of the anchoring stem makes it possible to obtain a solid and durable intramedullary connection in the top of the branch of the patient's mandible.

The design of the condylar prosthesis according to the invention, and more particularly the anchoring stem making it possible to use an intramedullary connection between the mandibular implant and the bony tissue, allows:

A reduction in the bone resection required for the elimination of the pathological natural condyle, which facilitates an optional surgical intervention, A decreasing of the duration of the surgical intervention and a reduction in the qualitative evaluations allowed to the surgeon during the positioning of the mandibular implant, such as the angular position of the implant, and the number, the type, and the distribution of screws, etc., An elimination of the torque effect by situating the entire mandibular implant in a parasagittal plane and by opting for a head with spherical geometry to replace the condyle.

More generally, the condylar prosthesis according to the invention makes it possible to solve the problems encountered with the prostheses of the prior art, to provide true comfort for the patient, and to meet a continuously increasing medical need due to the growing stress in the young population and a simultaneous extension of the service life.

This invention also covers a complete prosthesis for a temporomandibular joint comprising a condylar prosthesis according to the invention.

Other characteristics and advantages will emerge from the following description of the invention, a description provided only by way of example, relative to the accompanying drawings, in which.

This invention relates to a condylar prosthesis 10 for a temporomandibular joint as is illustrated in FIG. 1.

In a known way, this condylar prosthesis 10 comprises a mandibular implant 12 designed to be made integral with the branch of a human mandible, as well as a joint head 16 designed to serve as a substitute mandibular condyle.

Figure 3:
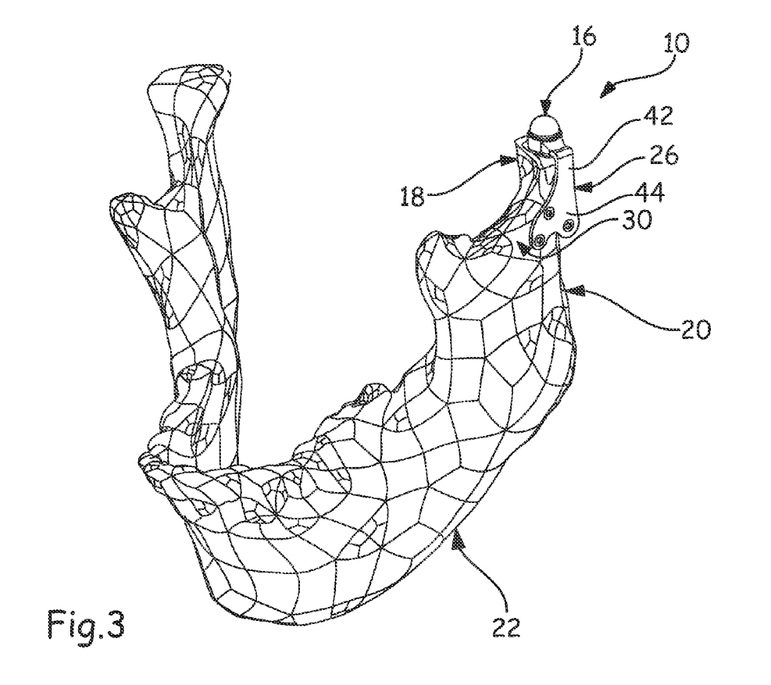
FIG. 3 shows a perspective view of the installation of a prosthesis according to the invention on a branch of a human mandible.

According to the invention and as FIG. 3 illustrates, the mandibular implant 12 comprises an anchoring stem 14 that makes possible the use of an intramedullary connection in the top 18 of the branch 20 of the mandible 22.

Thanks to this intramedullary connection and compared to the prostheses of the prior art, the load transfer from the joint head 16 to the bony tissue of the mandible 22 is not offset, and consequently, the joint head 16 does not undergo torque due to the engagement of the implant 12 in the mandible 22.

Hereinafter and relative to the orientation of the prosthesis 10 to the different figures, the median plane PM of the prosthesis 10 is a vertical plane containing the central longitudinal axis LC of the prosthesis and separating the mandibular implant 12 into two right and left parts. And, the frontal plane PF of the prosthesis 10 is a vertical plane containing the central longitudinal axis LC of the prosthesis, perpendicular to the median plane PM, and separating the mandibular implant 12 into two front and rear parts.

Figure 4:
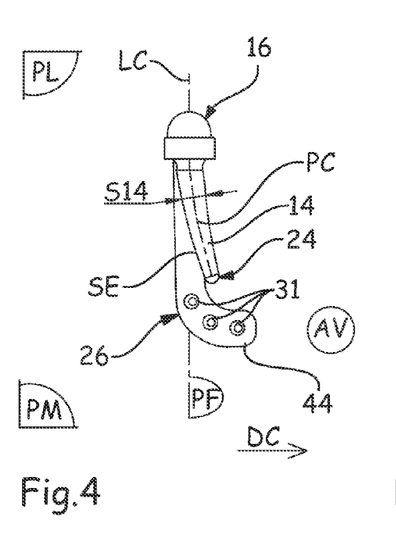
FIG. 4 shows a side view of a condylar prosthesis according to the invention.

Still for the purpose of improving the load transfer from the joint head 16 to the bony tissue of the mandible 22, and as illustrated by FIG. 4, the distal end 24 of the anchoring stem 14 is offset toward the front AV of the prosthesis 10 relative to the joint head 16 and in the median plane PM of the prosthesis 10.

In a preferred embodiment of the anchoring stem 14 whose purpose is to better distribute the forces in the mandibular branch 20 and to avoid the unstressed zones, the anchoring stem 14 follows a curved profile PC in its length L14 and in the median plane PM of the prosthesis, with the direction of curvature DC of the anchoring stem 14 being oriented toward the front AV of the prosthesis.

Advantageously, this curvature of the anchoring stem 14 also makes it possible to prevent a rotation of the mandibular implant 12 relative to the mandibular branch 20 once the former is anchored in the latter.

Figure 5:
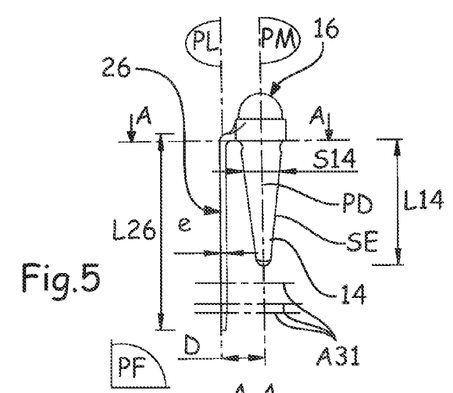
FIG. 5 shows a rear view of a condylar prosthesis according to the invention.

Still within a preferred embodiment of the anchoring stem 14 and so as to keep the forces originating from the joint head 16 essentially in the para-median plane of the mandibular branch 20, the anchoring stem 14 follows a straight profile PD in its length L14 and in the frontal plane PF of the prosthesis perpendicular to the median plane PM, as FIG. 5 illustrates it.

So as to facilitate the insertion of the anchoring stem 14 into the anchoring hole made in the top 18 of the mandibular branch 20 during the surgical intervention and to be able to anchor it loosely in this hole, the cross-section S14 of the anchoring stem 14 decreases in its length L14 and toward its distal end 24.

As FIGS. 4 and 5 illustrate, the cross-section S14 of the anchoring stem 14 preferably gradually decreases in its length L14 both in the median plane PM and in the frontal plane PF.

Figure 6:
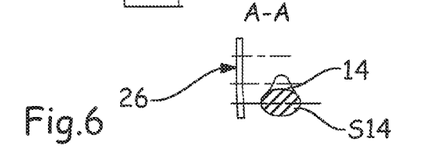
FIG. 6 shows a cutaway view along the line A-A of the rear view of a condylar prosthesis according to the invention shown in FIG. 5.

For the purpose of promoting a mechanical holding of the mandibular implant 12 in the anchoring hole made in the mandibular branch 20, and as the cutaway view illustrates in FIG. 6, the cross-section S14 of the anchoring stem 14 is preferably of the elliptical type in all or part of its length L14.

Because of the anatomy of the mandibular branch 20, the major axis of the ellipse is approximately parallel to the frontal plane PF of the prosthesis in the length L14 of the anchoring stem 14, while the minor axis of the ellipse is approximately parallel to the median plane PM of the prosthesis in the length L14 of the anchoring stem 14.

In a preferred embodiment of the anchoring stem 14, the anchoring stem 14 is of the elliptical type over its entire length L14, and its distal end 24 has a rounded, and preferably spherical, shape.

In a general manner, the invention covers a prosthesis 10 with an anchoring stem 14 with a non-circular cross-section S14 in all or part of its length L14, any non-circular shape making it possible for the cross-section S14 to prevent rotation and therefore to promote holding the mandibular implant 12 in the mandibular branch 20.

For the purpose of implementing the anchoring, the anchoring stem 14 has a rough, and preferably granular, outer surface SE that is treated and not shown in the figures, for increasing the intramedullary connection surface with the bony tissue of the mandibular branch 20 and for promoting the osteointegration of the mandibular implant 12 in the mandibular branch 20.

This rough or granular outer surface SE promotes the mechanical and biological anchoring of the implant 12 in the mandibular branch 20.

Advantageously, the bone fractures produced from mounting the anchoring stem 14 by force also reinforce the biological anchoring of the implant 12, and this is in addition to the specific coatings, in particular with a hydroxyapatite base, that are used for promoting bone reconstruction.

The roughness or the granular appearance of the outer surface SE of the anchoring stem 14 can be obtained by different mechanical processes, such as sandblasting, or by chemical attacks, with these processes being known to one skilled in the art.

Figure 9:
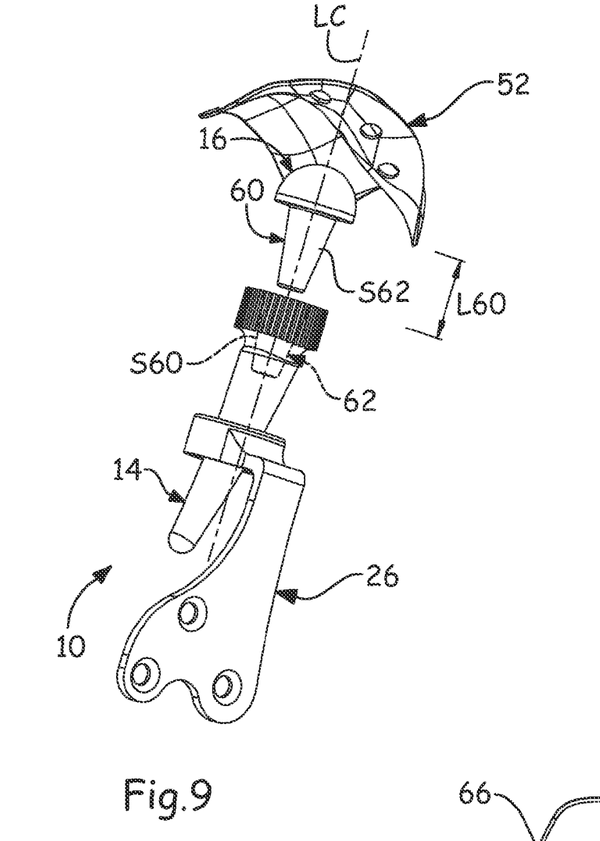
FIG. 9 shows a perspective and exploded side view of a complete prosthesis comprising a condylar prosthesis in an optimized embodiment according to the invention.

As FIG. 9 illustrates, in an optimized embodiment of the prosthesis 10 according to the invention, the body 28 of the mandibular implant 12 is made in two parts, with the joint head 16 being connected to the anchoring stem 14 of the mandibular implant 12.

For this purpose, the joint head 16 comprises a shrink-on stem 60, and the anchoring stem 14 comprises a receiving site 62 of this shrink-on stem 60.

More specifically, the shrink-on stem 60 extends under the joint head 16, and the receiving site 62 is hollowed-out in the anchoring stem 14 along the central longitudinal axis LC of the prosthesis.

Thanks to this embodiment in two parts of the mandibular implant 12, a set of different joint heads 16 with shrink-on stems 60 of different lengths L60 can be provided to the surgeon so that the latter selects the head 16 with the shrink-on length L60 that is the most suited to the patient's anatomy.

According to a first advantage, during an operation during which a large part of the top 18 of the mandibular branch 20 is to be removed because this part is diseased or too damaged, the surgeon can select a joint head 16 with a longer shrink-on stem 60, with the length L60 of the shrink-on stem 60 making it possible to compensate for the bone loss.

According to another advantage, during a surgical intervention operation, for example due to the growth of the mandibular branch 20 of the patient, the surgeon can only replace the joint head 16 and substitute it by a joint head 16 with a longer shrink-on stem 60. Thus, the surgeon can easily adapt the prosthesis 10 to the mandibular anatomy of the patient without removing the anchoring stem 14 in place and without stressing again the bony tissue of the mandibular branch 20 of the patient.

According to a last advantage, thanks to this embodiment in two parts of the mandibular implant 12, the joint head 16 can be made of a material that makes it possible to reduce friction, such as, for example, ceramic.

For the purpose of facilitating the assembly of the joint head 16 with the anchoring stem 14 and avoiding a screwed-in or glued connection, the receiving site 62 is conical.

In a preferred variant of the assembly of the joint head 16 with the anchoring stem 14, the shrink-on stem 60 and the receiving site 62 are conical, and their conical shrink-on surfaces S60 and S62 correspond to one another.

Thus, during an operation, the surgeon simply has to mount loosely by force the shrink-on stem 60 in the receiving site 62 to definitively assemble the joint head 16 with the anchoring stem 14.

In a minimal embodiment of the prosthesis according to the invention, the anchoring stem 14 that was just described may be sufficient to ensure the engagement of the implant 12 with the mandibular branch 20.

However, with the intramedullary connection between the implant 12 and the bony tissue of the mandibular branch 20 not being immediate, the patient should observe a convalescence period, which is longer the older the patient, after the surgical operation.

Also, in an optimized embodiment of the prosthesis according to the invention, the intramedullary connection allowed by the anchoring stem 14 is completed by an outer connection to the mandible 22, with this outer connection being designed in such a way as to be the least invasive possible and making it possible to hold the prosthesis 10 during the period of convalescence and reconstruction of the bony tissue around the anchoring.

For this purpose, and as illustrated in the different figures, the mandibular implant 12 also comprises an outer connection plate 26 that is integral with the body 28 of the prosthesis 10 formed by the anchoring stem 14 and the joint head 16.

With this connection plate 26 being designed to be attached to the lateral face 30 of the mandibular branch 20 using at least two, and preferably three, surgical screws 32, the connection plate 26 comprises at least two, and preferably three, emergent perforations 31 for the passage of surgical screws 32.

Preferably, the connection plate 26 can be shaped so as to be able to be adapted as well as possible to the bony anatomy of the patient's mandible.

The use of at least two surgical screws 32 makes it possible to prevent tilting or torsion of the joint head 16 around the central longitudinal axis LC of the prosthesis.

So as to avoid weakening the bony tissue around the anchoring, or stressing it too much, it is provided to offset the screws 32 relative to the anchoring stem 14.

For this purpose, the emergent perforations 31 are made around axes A31 that are offset relative to the anchoring stem 14 both in the frontal plane PF of the prosthesis and in the median plane PM of the prosthesis.

However, the emergent perforations 31 are not too removed from the anchoring stem 14, by only a few millimeters to provide an order of magnitude, so as to prevent too large a spacing relative to the loading point constituted by the joint head 16.

In a preferred embodiment of the prosthesis 10 whose purpose is to allow the installation of the anchoring in a first step and the outer attachment in a second step, the outer connection plate 26 is connected in a removable manner to the body 28 of the prosthesis 10.

Advantageously, this removable connection also allows the surgeon to choose whether or not to use the outer connection plate 26.

In a preferred variant embodiment of this removable connection, the outer connection plate 26 comprises an annular-type part 34 for engagement with the body 28 of the prosthesis, and the body 28 of the prosthesis comprises a cylindrical tooth bearing 36 for receiving the annular part 34 of the outer connection plate 26.

More specifically, the connection plate 26 extends under the annular part 34, and the cylindrical tooth bearing 36 is located between the joint head 16 and the anchoring stem 14.

So as to immobilize the outer connection plate 26 in rotation around the body 28 of the prosthesis, the outer surface S36 of the cylindrical tooth bearing 36 and the inner surface S34 of the annular part 34 comprise at least one hollow imprint 38 and a shape in relief 40 that can work with one another.

Figure 2:
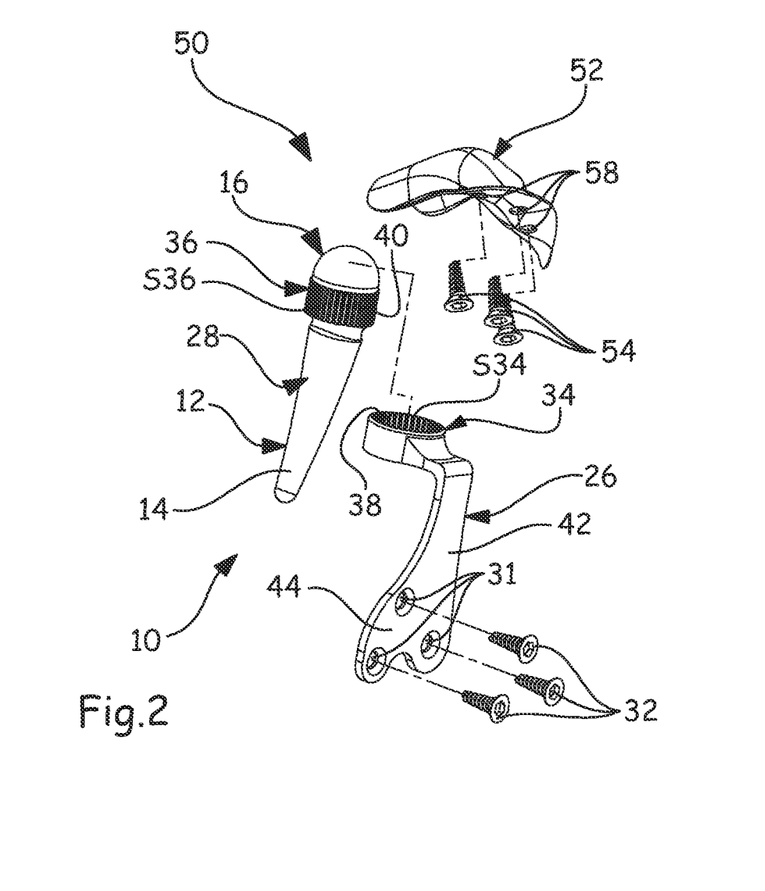
FIG. 2 shows a perspective and exploded view of a complete prosthesis comprising a condylar prosthesis according to the invention.

According to a first variant that is illustrated in FIG. 2, the cylindrical tooth bearing 36 and the inner surface S34 of the annular part 34 comprise a number of hollow imprints 38 and shapes in relief 40 to make it possible for the surgeon to orient the outer connection plate 26 around the body 28 of the prosthesis in the manner most suited to the mandibular anatomy of the patient.

Figure 10:
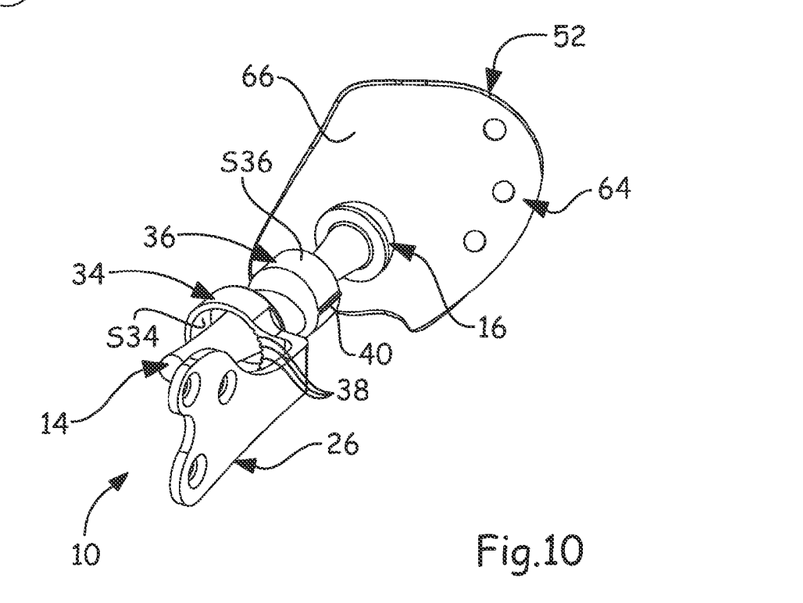
FIG. 10 shows a perspective and exploded bottom view of a complete prosthesis comprising a condylar prosthesis in an optimized embodiment according to the invention.

According to another variant that is illustrated in FIG. 10 and whose purpose is to simplify the production and to reduce production costs, the cylindrical tooth bearing 36 and the inner surface S34 of the annular part 34 comprise several hollow imprints 38, preferably five or six, and a unique shape in relief 40 to orient and to lock the outer connection plate 26 in rotation around the body 28 of the prosthesis.

In one or the other of the preceding variants, the hollow imprint(s) 38 is (are) provided in the inner surface S34 of the annular part 34 and the shape(s) in relief 40 is (are) provided on the outer surface S36 of the cylindrical tooth bearing 36.

Still in one or the other of the preceding variants, the hollow imprint(s) 38 and the shape(s) in relief 40 are obtained by knurling, by machining a groove-tab-type connection, etc.

Of course, so as to be positioned beyond the thickness of the bony tissue of the top 18 of the mandibular branch 20 prepared for receiving the prosthesis 10 according to the invention, the outer connection plate 26 is located in a lateral plane PL that is offset by a non-zero distance D relative to the median plane PM of the prosthesis in the frontal plane PF of the prosthesis.

Thanks to the number of hollow imprints 38 and shapes in relief 40, the parallel lateral plane PL can be arranged parallel to the median plane PM, or the surgeon can choose to slightly incline the lateral plane PL of the connection plate 26 relative to the median plane PM of the prosthesis if this is better suited to the mandibular anatomy of the patient.

To obtain an offsetting of the screws 32 relative to the anchoring stem 14, the outer connection plate 26 can assume essentially the shape of an L.

More specifically, with the vertical branch 42 of the L formed by the connection plate 26 extending from the joint head 16 approximately in the same direction as the anchoring stem 14 and the horizontal branch 44 of the L formed by the connection plate 26 extending in the direction of curvature DC of the anchoring stem 14 in a median plane PM of the prosthesis, the emergent perforations 31 are located in the horizontal branch of the L.

In a first variant embodiment of the outer connection plate 26 illustrated in FIGS. 3 to 6, the length L26 of the connection plate 26 is greater than the length L14 of the anchoring stem 14, and the horizontal branch 44 of the L, and therefore the emergent perforations 31, are offset below the anchoring stem 14.

Figure 7:
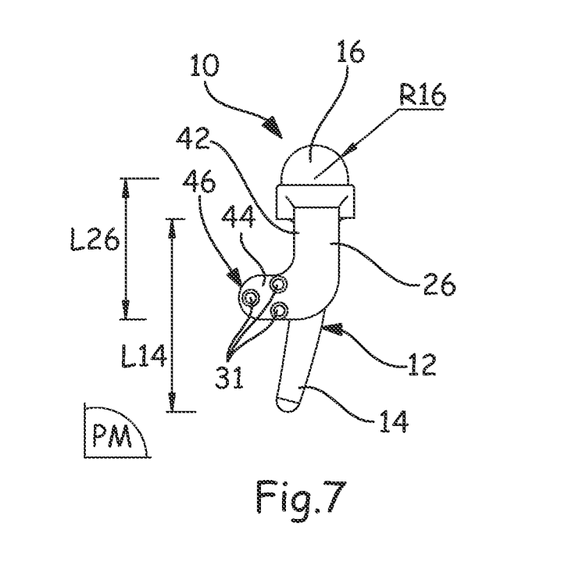
FIG. 7 shows a side view of a condylar prosthesis according to the invention that is equipped with a second variant of an outer connection plate.

In a second variant embodiment of the outer connection plate 26 illustrated in FIG. 7, the length L26 of the connection plate 26 is less than or equal to the length L14 of the anchoring stem 14, and the emergent perforations 31 are made in the end 46 of the horizontal branch 44 of the L extending in front of the anchoring stem 14.

Figure 8:
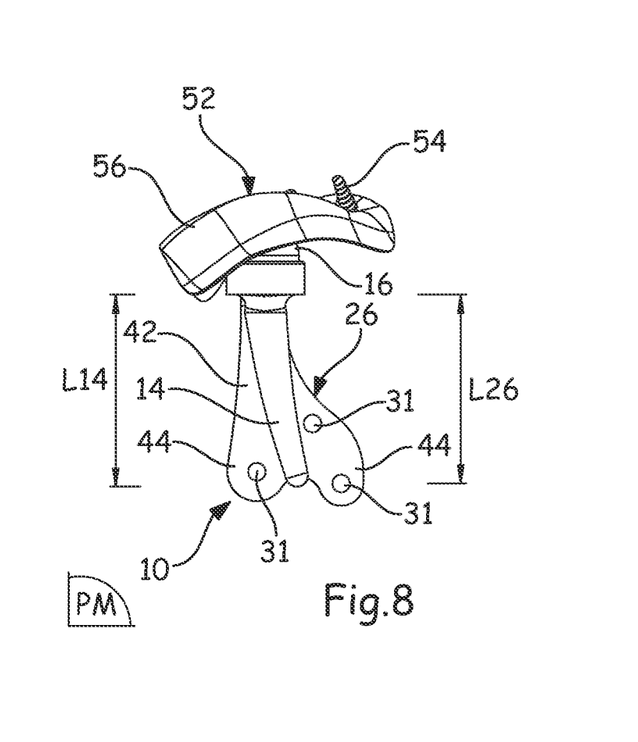
FIG. 8 shows a side view of a complete prosthesis with a condylar prosthesis according to the invention that is equipped with a third variant of an outer connection plate.

In a third variant embodiment of the outer connection plate 26 illustrated in FIGS. 2 and 8, with the length L26 of the connection plate 26 being approximately equal to the length L14 of the anchoring stem 14, the horizontal branch 44 of the L extends in front of and behind the anchoring stem 14, and the emergent perforations 31 are made in the horizontal branch 44 of the L in such a way as to be offset in front of and behind the anchoring stem 14.

In a known way, and as much in the design of the connection plate 26 as in that of the prosthesis 10, the angles and the ends of the different parts have rounded or beveled angles and/or rounded ends.

So as to limit the invasive aspect of the shapeable connection plate 26, in particular relative to the masseter muscle, the thickness e of the connection plate 26 is less than 0.8 millimeter.

This fineness of the connection plate 26 also makes it possible to avoid a significant bone resection for the installation of the prosthesis 10, which limits the amount of bone removed and therefore allows the possibility of surgical intervention.

Advantageously, and as indicated above, the fineness of the connection plate 26 also makes it possible for the surgeon to deform it to conform best to the bony anatomy of the patient's mandible.

By the same token, the length L14 of the anchoring stem 14 is around 30 millimeters, and the length L26 of the connection plate 26 varies between 12 and more than 30 millimeters according to its variant embodiment.

In a preferred embodiment whose purpose is to control the point of contact, and therefore the load, of the substitute condyle with the prosthetic element that replaces the fibrocartilaginous disc, the anchoring stem 14 is topped by a spherical joint head 16.

This spherical joint head 16 is centered around the central longitudinal axis LC of the prosthesis, and it has a radius of between 3 and 4.5 millimeters.

This invention also covers a complete prosthesis 50 for a temporomandibular joint integrating a condylar prosthesis 10 as was just described.

Such a complete prosthesis 50, illustrated by FIGS. 2 and 8, comprises a temporal prosthesis 52 designed to be attached to the skull, for example using surgical screws 54, and able to receive the joint head 16 of the condylar prosthesis 10.

For this purpose, the temporal prosthesis 52 assumes the shape of a plate 56 with an anatomical profile, of uniform thickness, and comprising different perforations 58.

Kinematically, the profile of the plate 56 makes it possible to transfer forces, with greatly reduced friction, through the center of the joint head 16 acting as a neocondyle and allows the joint head 16 to slide relative to the temporal prosthesis 52, both in the frontal plane PF and in the median plane PM.

Advantageously, the anatomical profile of the plate 56 is selected from among a representative panel of 3 to 5 anatomical profiles determined using a statistical study.

Thus, the delivery of several tens of temporal shells with each complete prosthesis is avoided, and the several anatomical profiles selected make it possible for the temporal prosthesis 52 to be adapted to the patients while coming close to each one's anatomical profile.

Preferably, the perforations 58 are located in the plate 56 in such a way as to make possible an implantation of the screws 54 in the thickest bony zone located close to the glenoid fossa.

Also, with the skull comprising two joints, right and left, the design of the condylar prosthesis 10 for a right or left temporomandibular joint is identical, only the outer connection plate 26 having to be exchanged for a symmetrical model relative to the median plane PM to be able to adapt the prosthesis 10 to the other joint.

Advantageously, and preferably in the case where the joint head 16 is made of a material that makes it possible to reduce friction, the lower surface 64 of the temporal prosthesis 52 on which the joint head 16 comes to rest is covered, at least in part, by a coating 66 of a material that also makes it possible to reduce friction, such as, for example, ceramic.

By reducing friction between the joint head 16 of the implant 12 and the temporal prosthesis 52, the vibrations and therefore the noise in the patient's head are limited, which is reflected by a better physiological comfort for the patient.

The invention claimed is:

1. A Condylar prosthesis (10) for a temporomandibular joint, with the condylar prosthesis (10) comprising:
    a mandibular implant (12) attachable with the branch (20) of a mandible (22),
    the mandibular implant (12) having a body (28) comprised of a joint head (16) connected to an anchoring stem (14), wherein,
        the joint head (16) is configured to serve as a substitute mandibular condyle,
        anchoring stem (14) makes possible the use of an intramedullary connection in the top (18) of the branch (20) of the mandible (22), with a distal end (24) of the anchoring stem (14) being offset toward the front (AV) of the prosthesis (10) relative to the joint head (16) and in a median plane (PM) of the prosthesis (10), and the anchoring stem (14) following a curved profile (PC) in its length (L14) and in the median plane (PM) of the prosthesis, with the direction of curvature (DC) of the anchoring stem (14) being oriented toward the front (AV) of the prosthesis, and
    the mandibular implant (12) further comprises an outer connection plate (26) that is integral with the body (28) of the mandibular implant (12), the connection plate (26) comprising at least two perforations (31) that emerge for the passage of surgical screws.

2. Condylar prosthesis (10) according to claim 1, wherein the anchoring stem (14) follows a straight profile (PD) in its length (L14) and in a frontal plane (PF) of the prosthesis that is perpendicular to the median plane (PM).

3. Condylar prosthesis (10) according to claim 1, wherein the cross-section (S14) of the anchoring stem (14) decreases in its length (L14) and toward its distal end (24).

4. Condylar prosthesis (10) according to claim 1, wherein the cross-section (S14) of the anchoring stem (14) is not circular in all or part of its length (L14).

5. Condylar prosthesis (10) according to claim 4, wherein the cross-section (S14) of the anchoring stem (14) is of the elliptical type in all or part of its length (L14), with the major axis of the ellipse being parallel to the frontal plane (PF) of the prosthesis in the length (L14) of the anchoring stem (14), and with the minor axis of the ellipse being parallel to the median plane (PM) of the prosthesis in the length (L14) of the anchoring stem (14).

6. Condylar prosthesis (10) according to claim 1, wherein the anchoring stem (14) has a rough or granular outer surface (SE) for increasing the intramedullary connection surface and for promoting the osteointegration of the mandibular implant (12) in the mandibular branch (20).

7. Condylar prosthesis (10) according to claim 1, wherein the outer connection plate (26) least two perforations (31) have axes (A31) that are offset relative to the anchoring stem (14) both in the frontal plane (PF) of the prosthesis and in the median plane (PM) of the prosthesis.

8. Condylar prosthesis (10) according to claim 7, wherein the thickness (e) of the connection plate (26) is less than 0.8 millimeter.

9. Condylar prosthesis (10) according to claim 1, wherein the outer connection plate (26) is shapable to be adapted to bony anatomy of a patient's mandible.

10. Condylar prosthesis (10) according to claim 1, wherein the outer connection plate (26) is connected in a removable manner to the body (28) of the prosthesis (10).

11. Condylar prosthesis (10) according to claim 10, wherein the outer connection plate (26) comprises an annular-type part (34) for engagement with the body (28) of the prosthesis, and wherein the body (28) of the prosthesis comprises a cylindrical tooth bearing (36) for receiving the annular part (34) of the outer connection plate (26), with the connection plate (26) extending under the annular part (34), the cylindrical tooth bearing (36) being between the joint head (16) and the anchoring stem (14), and the outer surface (S36) of the cylindrical tooth bearing (36) and the inner surface (S34) of the annular part (34) comprising at least one hollow imprint (38) and a shape in relief (40) that can work with one another to immobilize the outer connection plate (26) in rotation around the body (28) of the prosthesis.

12. Condylar prosthesis (10) according to claim 1, wherein the outer connection plate (26) is located in a lateral plane (PL) that is offset by a non-zero distance (D) relative to the median plane (PM) of the prosthesis in the frontal plane (PF) of the prosthesis.

13. Condylar prosthesis (10) according to claim 1, wherein with the outer connection plate (26) assuming approximately the shape of an L whose vertical branch (42) extends from the joint head (16) essentially in the same direction as the anchoring stem (14) and whose horizontal branch (44) extends in the direction of curvature (DC) of the anchoring stem (14) in a median plane (PM) of the prosthesis, the emergent perforations (31) are located in the horizontal branch (44) of the L.

14. Condylar prosthesis (10) according to claim 13, wherein the length (L26) of the connection plate (26) is greater than the length (L14) of the anchoring stem (14), and wherein the horizontal branch (44) of the L, and therefore the emergent perforations (31), are offset below the anchoring stem (14).

15. Condylar prosthesis (10) according to claim 13, wherein the length (L26) of the connection plate (26) is less than or equal to the length (L14) of the anchoring stem (14), and wherein the emergent perforations (31) are made toward the end (46) of the horizontal branch (44) of the L extending in front of the anchoring stem (14).

16. Condylar prosthesis (10) according to claim 13, wherein with the length (L26) of the connection plate (26) being approximately equal to the length (L14) of the anchoring stem (14), the horizontal branch (44) of the L extends in front of and behind the anchoring stem (14), and the emergent perforations (31) are made in the horizontal branch (44) of the L in such a way as to be offset in front of and behind the anchoring stem (14).

17. Condylar prosthesis (10) according to claim 1, wherein the body (28) of the mandibular implant (12) is made in two parts, with the joint head (16) being connected to the anchoring stem (14) of the mandibular implant (12).

18. Condylar prosthesis (10) according to claim 17, wherein the joint head (16) comprises a shrink-on stem (60) and wherein the anchoring stem (14) comprises a site (62) for receiving this shrink-on stem (60).

19. A condylar prosthesis (10) for a temporomandibular joint, with the condylar prosthesis (10) comprising:
   a mandibular implant (12), attachable with the branch (20) of a mandible (22), and
   a joint head (16), designed to serve as a substitute mandibular condyle, with the mandibular implant (12) comprising an anchoring stem (14) making possible the use of an intramedullary connection in the top (18) of the branch (20) of the mandible (22), and with a distal end (24) of the anchoring stem (14) being offset toward the front (AV) of the prosthesis (10) relative to the joint head (16) and in a median plane (PM) of the prosthesis (10),
   wherein the anchoring stem (14) follows a curved profile (PC) in its length (L14) and in the median plane (PM) of the prosthesis, with the direction of curvature (DC) of the anchoring stem (14) being oriented toward the front (AV) of the prosthesis, and
   wherein the anchoring stem (14) is topped by a spherical joint head (16).

20. A complete prosthesis (50) for a temporomandibular joint, comprising:
   a temporal prosthesis (52); and
   a condylar prosthesis (10) comprising
   a mandibular implant (12), attachable with the branch (20) of a mandible (22), and
   a joint head (16), designed to serve as a substitute mandibular condyle, with the mandibular implant (12) comprising an anchoring stem (14) making possible the use of an intramedullary connection in the top (18) of the branch (20) of the mandible (22), and with a distal end (24) of the anchoring stem (14) being offset toward the front (AV) of the prosthesis (10) relative to the joint head (16) and in a median plane (PM) of the prosthesis (10),
   wherein the anchoring stem (14) follows a curved profile (PC) in its length (L14) and in the median plane (PM) of the prosthesis, with the direction of curvature (DC) of the anchoring stem (14) being oriented toward the front (AV) of the prosthesis.

21. Condylar prosthesis (10) according to claim 20, wherein the joint head (16) is made of a material that makes it possible to reduce friction and wherein the lower surface (64) of the temporal prosthesis (52) is covered, at least in part, by a coating (66) of a material making it possible to reduce friction.

* * * * *